United States Patent [19]

Abiko et al.

[11] Patent Number: 5,602,123
[45] Date of Patent: Feb. 11, 1997

[54] THERAPEUTIC AGENT FOR MYOCARDIAL ISCHEMIC DAMAGES OR REPERFUSION

[75] Inventors: Yasushi Abiko; Hiroko Hashizume; Akiyoshi Hara, all of Asahikawa; Yoichi Yamauchi, Komae; Junichi Kawagoe, Sayama, all of Japan

[73] Assignee: Kowa Co., Ltd., Nagoya, Japan

[21] Appl. No.: 548,678

[22] Filed: Oct. 26, 1995

[30] Foreign Application Priority Data

Nov. 2, 1994 [JP] Japan .................................. 6-269503

[51] Int. Cl.$^6$ .................................................. A61K 31/55
[52] U.S. Cl. ............................................................. 514/218
[58] Field of Search .............................................. 514/218

[56] References Cited

U.S. PATENT DOCUMENTS 5,389,630  2/1995  Sato et al. ............................... 514/218

FOREIGN PATENT DOCUMENTS 0541798  5/1993  European Pat. Off. .
1452413  10/1976  United Kingdom .

OTHER PUBLICATIONS

Japanese Journal of Pharmacology, vol. 67, No. S1, p. 121P, Mar. 1995, A. N. Hoque, et al., "Cardioprotective Effect of K-7259, A New Delazep Derivative, in the Ischemic-Reperfused Isolated Working Rat Hearts".

Japanese Journal of Pharmacolgy, vol. 59, No. S1, p. 256P, 1992, Y. Yamauchi, et al., "Neuroprotective Effects of K-7259 Against Cerebral Anoxia and Ischemia".

The Kurume Medical Journal, vol. 41, No. 3, pp. 123–130, 1994, M. Tsurusaki, et al., "Effects of K-7259 on Neuronal Activity and Synaptic Transmission in the Rat Dorsolateral Septal Nucleus".

Martindale, The Extra Pharmacopoeia, p. 1019, 1993, J. E. F. Reynolds, "Dilazep Hydrochloride".

Arneimittelforschung/Drug Research, vol. 35, No. 12, pp. 1802–1804, 1985, S. Sugiyama, et al., "The Effects of Dilazep on Reperfusion Arrhythmias".

STN File Supplier: Medline AN-90284804, 1990, Y. Yamauchi, et al., "Effect of Dilazep Dihydrochloride on Ischemia and Reperfusion–Induced Cerebral Injury in Spontaneously Hypertensive Rats" (Abstract Only).

K. Ichihara et al, Journal of Cardiovascular Pharmacology, "Effects of Diltiazem and Propranolol on Irreversibility of Ischemic Cardiac Function and Metabolism in the Isolated Perfused Rat Heart", vol. 5, pp. 745–751, (1983).

Primary Examiner—Raymond Henley, III
Attorney, Agent, or Firm—Oblon, Spivak, McClelland, Maier & Neustadt, P.C.

[57] ABSTRACT

A therapeutic agent for myocardial ischemic damages or reperfusion injuries which contains, as an active ingredient, a compound of the following formula (1), an acid addition salt thereof, or a hydrate thereof:

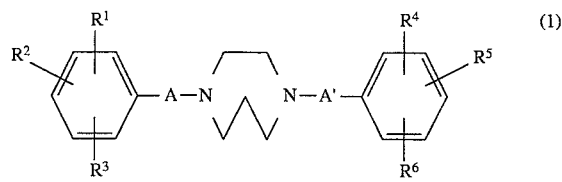

wherein $R^1$ to $R^6$ are lower alkoxy groups and A and A' are lower alkylene groups; a method for treating those disorders which uses the above compound; and use of the compound in the manufacture of such a therapeutic agent. The therapeutic agent has an excellent action of recovering lowered heart functions caused by myocardial ischemia-reflow, and have low toxicity.

2 Claims, 1 Drawing Sheet

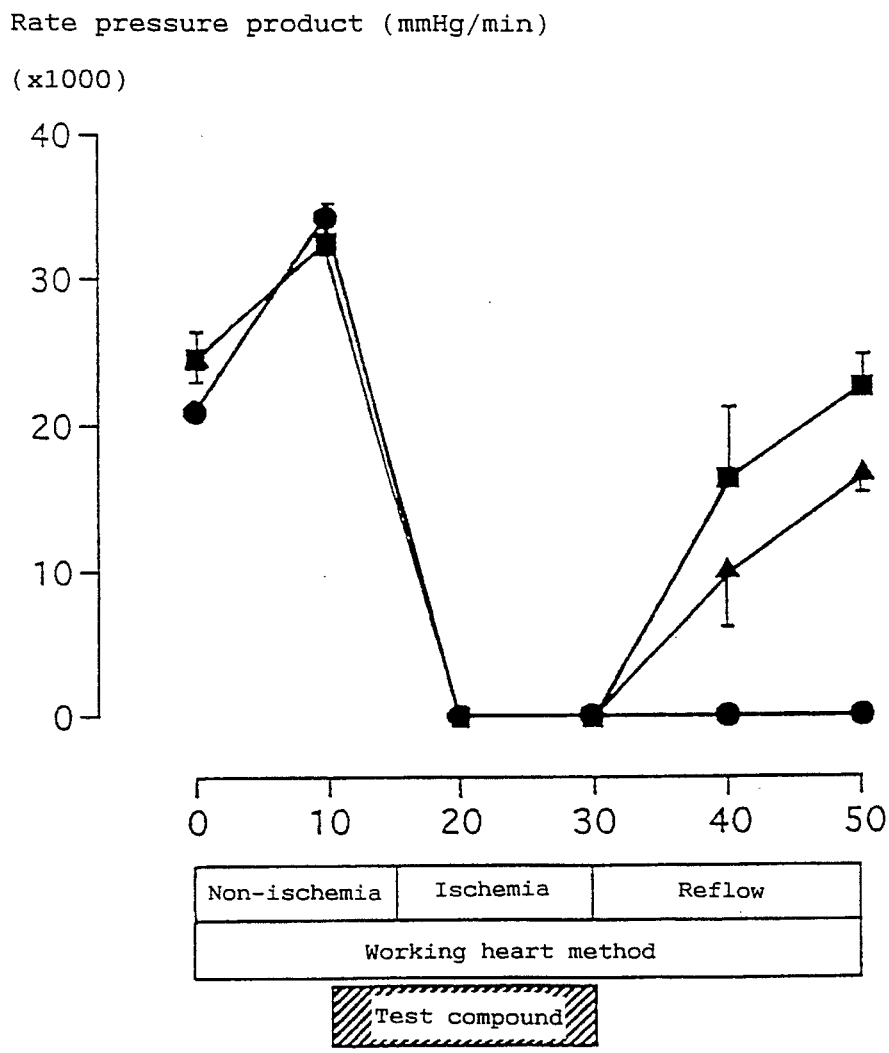

THERAPEUTIC AGENT FOR MYOCARDIAL ISCHEMIC DAMAGES OR REPERFUSION

BACKGROUND OF THE INVENTION

1) Field of the Invention

The present invention relates to therapeutic agents for myocardial ischemic damages or reperfusion injuries which have excellent action for restoring heart functions lowered by myocardial ischemia or reflow.

2) Background Art

In open heart surgery including heart transplant, an aortic blockade is useful and even essential since it provides an excellent setting in terms of surgical techniques, including a bloodless and stationary field of view.

However, due to the stoppage of coronary blood flow during an operation, myocardial cells rapidly become to undergo anaerobic metabolism in which energy production efficiency is very poor. Subsequently, accumulation of lactic acid and hydrogen ions generated in the course of anaerobic metabolism reduces pH in tissues and suppresses oxidation of fatty acids, thereby causing damage to mitochondria. As a result, myocardial cells have disorders in energy-dependent cell membrane functions, and these disorders impair the equilibration ability and cell capacity maintenance ability of cytoplasms. In addition, calcium ions abnormally flow into cells, inviting sodium ions and water into the cells. Eventually, myocardial cells come to have irreversible ischemic damages.

In order to prevent the above-mentioned myocardial ischemic damages, it is essential that high energy substances in heart muscles be retained during ischemia. Presently, a protection method for heart muscles is used which is primarily a combination of a local cooling method for heart muscles and a method of multi-administration of a myocardial preservation solution in which a myocardial preservation solution is intermittently administered to the patient.

However, this method still cannot satisfactorily prevent myocardial ischemic damages.

On the other hand, although ischemic heart muscles recover from the low energy state when an aortic blockade is removed after a heart operation, reflow of blood after ischemia is known to cause even worse disorders called reperfusion injuries. Reperfusion injuries are considered to be caused primarily by changes in membranes during ischemia which trigger the reflow. Within an early stage of 2–3 minutes from the start of reflow, abnormal transfer of calcium ions as well as sodium ions and water occurs, and oxygen radicals are generated. In order to prevent reperfusion injuries, useful compounds have been studied in adition to a careful blood flow restarting method which requires a high skill. However, successful results have not yet been obtained in preventing reperfusion injuries.

The onset of heart infarction is considered to be triggered by a repeated blockade of the coronary artery and subsequent reflow caused, for example, by atherosclerosis and thrombus. In this case, heart muscles undergo ischemic damages and reperfusion injuries. In the therapy of heart infarctions, percutaneous transluminal coronary angioplasty (PTCA) in which balloons are used for dilating the inner diameter of the coronary artery or percutaneous transluminal coronary recanalization (PTCR) in which a thrombolytic agent is administered through a catheter are adopted, and favorable results have been obtained. However, these approaches are still not free from reflow disorders.

Under the above circumstances, the present inventors conducted earnest studies to discover drugs capable of suppressing those disorders, and as a result, found that the compounds represented by the following formula (1), their acid addition salts, and their hydrates have an action of restoring heart functions which were lowered by ischemia-reflow of heart muscles, and that these compounds, salts, and hydrates are useful as therapeutic agents for myocardial ischemic damages and reperfusion injuries. The present invention was accomplished based on this finding.

SUMMARY OF THE INVENTION

Accordingly, an object of the present invention is to provide a drug which suppresses myocardial ischemic damages and reperfusion injuries and which accelerates the post-operative recovery of heart functions.

In one aspect of the present invention, there is provided a therapeutic agent for myocardial ischemic damages or reperfusion injuries which comprises, as an active ingredient, a compound of the following formula (1), an acid addition salt thereof, or a hydrate thereof:

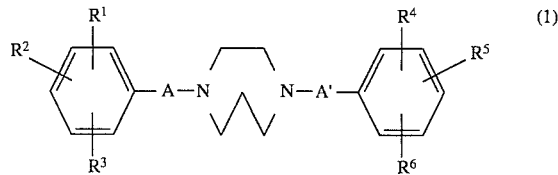

wherein $R^1$, $R^2$, $R^3$, $R^4$, $R^5$ and $R^6$ are identical to or different from each other, and each represent a lower alkoxy group, and A and A' are identical to or different from each other and each represent a lower alkylene group.

In another aspect of the present invention, there is provided a method for treating myocardial ischemic damages or reperfusion injuries which includes administering an effective amount of the above compound to a patient with myocardial ischemic damages or reperfusion injuries.

In a further aspect of the present invention, there is provided a use of the above compound in the manufacture of a therapeutic agent for myocardial ischemic damages or reperfusion injuries.

The above and other objects, features, and advantages of the present invention will become apparent from the following description.

BRIEF DESCRIPTION OF THE DRAWINGS

A sole FIGURE is a graph which shows an action of restoring heart functions which were lowered by myocardial ischemia and subsequent reflow.

DETAILED DESCRIPTION OF PREFERRED EMBODIMENTS

Compounds of the aforementioned formula (1) (hereinafter referred to as compounds (1)) which are used in the present invention are already known. For example, they are described in EP541798A. This publication describes that these compounds are useful as brain protecting agents for ameliorating disorders of brain functions such as brain hemorrhage, brain infarction, subarachnoidal hemorrhage, transient cerebral ischemic attack, and cerebrovascular disorders, or preventing the progress of such disorders. However, this publication does not suggest anything as to whether the compounds are applicable to myocardial ischemic damages and reperfusion injuries.

In formula (1), the lower alkoxy groups represented by $R^1$ to $R^6$ have preferably 1 to 6 carbon atoms. Particularly, methoxy, ethoxy, n-propoxy, and isopropoxy are preferred. The lower alkylene groups represented by A and A' are preferably $C_1$–$C_6$ linear or branched alkylene groups, and more preferably $C_3$–$C_5$ alkylene groups. Particularly, n-propylene, n-butylene, and n-pentylene are preferred.

Among the compounds (1), preferable ones are those in which $R^1$ to $R^6$ are methoxy and A and A' are butylene. Particularly, N,N'-bis-[4-(3,4,5-trimethoxyphenyl)butyl]homopiperazine is preferred.

The compounds (1) can be prepared by the method described for example in EP541798A, and preferably by the method (1) described in this publication.

In the present invention, acid addition salts or hydrates of compounds (1) may also be used. Acid addition salts can be prepared by a routine method. As examples of the acids which are used for preparing the acid addition salts, there are inorganic acids such as sulfuric acid, hydrochloric acid, nitric acid, phosphoric acid, and hydrobromic acid; and organic acids such as acetic acid, lactic acid, succinic acid, tartaric acid, malic acid, maleic acid, citric acid, fumaric acid, methanesulfonic acid, and toluenesufonic acid.

The therapeutic agents according to the present invention contain compounds (1), acid addition salts thereof, or hydrates thereof as their active ingredients.

These active ingredients are used singly or in combination with pharmaceutically acceptable excipients, binders, carriers, diluents, etc. and formulated into tablets, capsules, granules, powders, injections, or suppositories. These formulations can be prepared by known methods. For example, in order to prepare formulations for oral administration, compounds (1) are blended together with excipients such as starch, mannitol, and lactose; binders such as carboxymethylcellulose-Na and hydroxypropylcellulose; disintegrators such as crystalline cellulose and carboxymethylcellulose-Ca; lubricants such as talc and magnesium stearate; and fluidity improvers such as light silicic acid anhydride.

The dose of the compounds (1) of the present invention varies depending on the patient's body weight, age, sex, conditions, etc. In general, a dose from 0.1 to 1,000 mg/day is preferred for an adult, which is administered at a time or in 2–3 divided times. If the compounds (1) are used in an extracorporeal circulation, they are preferably controlled to have a concentration in a range from 1 nM to 1 mM.

Preferably, the therapeutic agents of the present invention are administered to patients which are going to have an aortic blockade or reflow in open heart surgery, PTCA, or PTCR, or patients who are currently undergoing such treatments in a systemic manner or by oral administration. Alternatively, the therapeutic agents may be added to extracorporeal circulation of such patients. To patients who are likely to have an onset of heart infarction, oral and systemic administrations are preferred. In the case of heart transplant, the therapeutic agents are administered to the donor and the recipient, and also to the preservation solution of the heart.

EXAMPLES

The present invention will be explained in more detail by the following examples, which should not be construed as limiting the present invention.

Preparation Example 1

Preparation of N,N'-bis-[4-(3,4,5-trimethoxyphenyl)butyl] homopiperazine.2 HCl:

1-Chloro-4-(3,4,5-trimethoxyphenyl)butane (7.5 g), homopiperazine (1.3 g), potassium carbonate (4.5 g), and potassium iodide (5.3 g) were added to dimethylformamide (4.2 ml), and the resulting mixture was stirred at 100° C. for 1 hour. The reaction mixture was poured into a NaCl solution, and then extracted with ethyl acetate. The ethyl acetate layer was extracted with dilute hydrochloric acid, and the aqueous layer was washed with ethyl acetate. The resulting material was made basic with NaOH, and extracted with ether. The ether layer was washed with a NaCl solution and dried. The solvent was distilled off. The residue was purified by silica gel column chromatography. A free base was obtained in an amount of 4.7 g.

This product was converted to a hydrochloride by a routine method, and recrystallized from methanol-ether, obtaining 3.2 g of the title compound having a melting point of 191°–194° C. (decomposition).

$^1$H-NMR (CDCl$_3$); δ 2.60 (4H, br, t, J=8 Hz) 3.82 (6H,s) 3.86 (12H,s) 6.37 (4H,s) IR (KBr); cm$^{-1}$ 1587, 1238, 1122

Example 1

Action of Restoring Heart Functions Which Were Lowered By Myocardial Ischemia-Reflow Effects of N,N'-bis-[4-(3,4,5-trimethoxyphenyl)butyl]homopiperazine.2 HCl (hereinafter referred to as the test compound) on heart functions lowered by myocardial ischemia-reflow were investigated using a rat reflow heart model.

By using a Langendorff method and a working heart method on rats, a reflow heart model was established. Changes in heart functions were checked using a rate pressure product (arterial blood pressure X pulse) [Ichihara and Abiko, J. Cardiovasc. Pharmacol., 5, 745–751 (1983)]. Fifteen minutes after applying a working heart method, the rats were forced to undergo an ischemia for 15 minutes and then reflow for 20 minutes. The test compound was dissolved in a perfusion liquid (Krebs-Henzelite sodium bicarbonate buffer) so as to have a concentration of 1 μM or 5 μM. The thus-prepared test solution was administered to the rats for 20 minutes starting from 5 minutes before the application of ischemic load to the removal of the load. A group of rats to which the test compound was not administered was used as a control, and the results obtained therefrom were compared with those obtained from the groups of rats to which the test compound was administered.

As shown in the accompanying sole FIGURE, in the control group (non-administration of the test compound), the rate pressure product decreased after application of the load of ischemia, and value 0 continued from 5 minutes after starting the application of the ischemic load to the end of the test, i.e., to 20 minutes after starting reflow. In the groups to which the test compound was administered, the rate pressure product decreased after the application of the load of ischemia like the non-administration group, and the rate reached 0 when 5 minutes were elapsed after the application of the ischemic load. However, when reflow was started, the rate pressure product gradually increased. When 20 minutes have passed from the start of reflow, the rate pressure product recovered by about 52% (1 μM administration) and about 69% (5 μM administration) compared with the value obtained at the time point of 10 minutes after application of the working heart method.

Accordingly, it was confirmed that the test compound has an action of restoring heart functions which were lowered by myocardial ischemia-reflow.

Example 2

Acute Toxicity Test

Groups of male slc:Wistar rats (about 10 week old), each consisting of 5 rats, were used. The test compound was suspended in 5% gum arabic, and 300 or 1,000 mg/kg of the suspension was orally administered to each rat. The behavior of the rats were observed at the time of 0.5, 1, 2, and 4 hours after administration. Thereafter, the animals were fed for further 3 days under observation.

As a result, the test compound was found to cause neither abnormal behavior nor death at both doses of 300 mg/kg and 1,000 mg/kg by oral administration.

Example 3

Capsules

| | |
|---|---|
| N,N'-bis-[4-(3,4,5-trimethoxyphenyl)-butyl]homopiperazine.2HCl | 30 mg |
| Microcrystalline cellulose | 30 mg |
| Lactose | 57 mg |
| Magnesium stearate | 3 mg |
| Total amount | 120 mg |

The above ingredients were mixed by a known method, and then charged in a gelatin capsule to obtain a capsulated agent.

Example 4

Tablets

| | |
|---|---|
| N,N'-bis-[4-(3,4,5-trimethoxyphenyl)-butyl]homopiperazine.2HCl | 30 mg |
| Starch | 44 mg |
| Starch powder (for pastes) | 5.6 mg |
| Magnesium stearate | 0.4 mg |
| Carboxymethylcellulose-Ca | 20 mg |
| Total amount | 100 mg |

The above ingredients were mixed by a known method to obtain a tablet.

Example 5

Injection Liquids

N,N'-bis-[4-(3,4,5-trimethoxyphenyl)butyl]homopiperazine.2 HCl (100 mg) and NaCl (900 mg) were dissolved in about 80 ml of distilled water for injection and to the resulting solution, distilled water for injection was added to make the total amount 100 ml. The resulting solution was aseptically filtered and dispensed into 10 light-shielded ampules. The ampules were sealed to obtain an aseptic injection liquid.

As described above, the therapeutic agents of the present invention have an excellent action of restoring lowered heart functions caused by myocardial ischemia-reflow, and have low toxicity. Thus, they are useful as therapeutic agents for myocardial ischemic damages or reperfusion injuries.

What is claimed is:

1. A method for restoring lowered heart function caused by myocardial ischemia-reperfusion, which comprises administering to a patient suffering from said lowered heart function an effective amount of a compound of the following formula (1), an acid addition salt thereof, or a hydrate thereof:

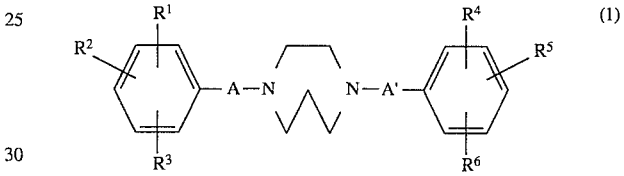

wherein $R^1$, $R^2$, $R^3$, $R^4$, $R^5$ and $R^6$ are identical to or different from each other, and each represent a lower alkoxy group, and A and A' are identical to or different from each other and each represent a lower alkylene group.

2. The method of claim 1, which comprises administering N,N'-bis-[4-(3,4,5-trimethoxyphenyl)butyl]homopiperazine, an acid addition salt thereof, or a hydrate thereof.

* * * * *

UNITED STATES PATENT AND TRADEMARK OFFICE
CERTIFICATE OF CORRECTION

PATENT NO.   : 5,602,123
DATED        : February 11, 1997
INVENTOR(S)  : Yasushi ABIKO, et al.

It is certified that error appears in the above-indentified patent and that said Letters Patent is hereby corrected as shown below:

On the title page, Item [54] and the top of column 1, the title should read:

--THERAPEUTIC AGENT FOR MYOCARDIAL ISCHEMIC DAMAGES OR REPERFUSION INJURIES--

Signed and Sealed this

Twenty-ninth Day of April, 1997

Attest:

BRUCE LEHMAN

*Attesting Officer*         *Commissioner of Patents and Trademarks*